US010441712B2

(12) United States Patent
Morlok et al.

(10) Patent No.: US 10,441,712 B2
(45) Date of Patent: Oct. 15, 2019

(54) CONTINUOUS INFUSION DEVICE (71) Applicant: H & B Electronic GmbH & Co. KG, Deckenpfronn (DE)

(72) Inventors: Tobias Morlok, Motzingen (DE); Wilfried Weber, Schopfloch (DE)

(73) Assignee: H & B ELECTRONIC GMBH & CO. KG, Deckenpfronn (DE)

( * ) Notice: Subject to any disclaimer, the term of this patent is extended or adjusted under 35 U.S.C. 154(b) by 436 days.

(21) Appl. No.: 14/914,104

(22) PCT Filed: Jan. 9, 2015

(86) PCT No.: PCT/EP2015/000025
§ 371 (c)(1),
(2) Date: Jul. 11, 2016

(87) PCT Pub. No.: WO2015/124247
PCT Pub. Date: Aug. 27, 2015

(65) Prior Publication Data
US 2016/0303317 A1 Oct. 20, 2016

(30) Foreign Application Priority Data

Feb. 19, 2014 (DE) .................... 20 2014 001 525 U (51) Int. Cl.
*A61M 5/142* (2006.01)
*A61M 5/38* (2006.01)
(Continued)

(52) U.S. Cl.
CPC .......... *A61M 5/142* (2013.01); *A61M 5/1454* (2013.01); *A61M 5/168* (2013.01);
(Continued)

(58) Field of Classification Search
CPC ...... A61M 2005/1657; A61M 5/3145–5/3146; A61M 5/168; A61M 5/383;
(Continued)

(56) References Cited

U.S. PATENT DOCUMENTS 4,059,110 A 11/1977 Wuthrich et al.
6,309,375 B1 * 10/2001 Glines ................ A61B 17/3478
604/187

(Continued)

FOREIGN PATENT DOCUMENTS

DE 1491747 C2 5/1974
DE 2410868 A1 9/1974
(Continued)

*Primary Examiner* — Nathan R Price
*Assistant Examiner* — Melissa A Snyder
(74) *Attorney, Agent, or Firm* — Browdy and Neimark, P.L.L.C.

(57) ABSTRACT

A device (2) for continuous infusions has a housing (4) in which an infusion appliance seat (6) is provided for receiving an infusion appliance (18) with at least one container (22) that can be pressed empty by means of a ram (20), which infusion appliance seat (6) extends along a main axis of extent (AA) from a ram-side end (26) to an outlet-side end (28). The continuous infusion device (2) moreover has an actuator (30) for automatically emptying the infusion appliance (18), a drive (32) for moving a ram abutment/actuation element (24) of the actuator (30), and a control arrangement (72) by means of which a speed of advance of the actuator (30) is adjustable. Provision is made here that the main axis of extent (AA) of the infusion appliance seat (6) has a predetermined relief angle (W) in relation to a support plane (E) of the housing (4), and here the outlet-side end (28) is arranged above the ram-side end (26) of the infusion appliance seat (6).

18 Claims, 7 Drawing Sheets (51) Int. Cl.
 *A61M 5/145* (2006.01)
 *A61M 5/168* (2006.01)

(52) U.S. Cl.
 CPC .......... *A61M 5/385* (2013.01); *A61M 5/1456* (2013.01); *A61M 2005/14506* (2013.01)

(58) Field of Classification Search
 CPC ...... A61M 5/1456; A61M 2005/14506; A61M 5/14546; A61M 5/007; A61M 5/008; A61M 5/20
 See application file for complete search history.

(56) References Cited

U.S. PATENT DOCUMENTS

| | | | |
|---|---|---|---|
| 7,018,360 B2 * | 3/2006 | Flaherty | A61M 5/14248 604/123 |
| 2005/0148868 A1 | 7/2005 | Fago et al. | |
| 2013/0131589 A1 * | 5/2013 | Mudd | A61M 5/19 604/82 |

FOREIGN PATENT DOCUMENTS

| | | |
|---|---|---|
| DE | 69721316 T2 | 2/2004 |
| DE | 60131653 T2 | 10/2008 |
| DE | 202013000411 U1 | 1/2013 |
| WO | 2013051115 A1 | 4/2013 |

* cited by examiner

CONTINUOUS INFUSION DEVICE

The invention relates to a device for continuous infusions, such as for example for the administration of drugs against multiple sclerosis, according to the preamble to claim 1, and to an infusion arrangement with such a device. In this case the continuous infusion device has a housing in which an infusion appliance seat is provided for receiving an infusion appliance with at least one container that can be pressed empty by means of a ram, which infusion appliance seat extends along a main axis of extent from a ram-side end to an outlet-side end. Moreover, the continuous infusion device has an actuator for automatically emptying the infusion appliance. The actuator in turn has a ram abutment/actuation element, which can be displaced by means of a mechanical drive. Furthermore, a control arrangement is provided, by means of which a speed of advance of the actuator device can be adjusted.

With such continuous infusion devices, regardless of location it is possible for the smallest infusion flows of a drug to be administered continuously over several hours into the bloodstream of a patient. This enables a very flexible and, for example, mobile use of the devices.

U.S. Pat. No. 4,059,110 patent discloses an infusion device, by means of which a specified quantity of a liquid drug can be administered over a predetermined time period from a syringe via an infusion line. For this purpose, the infusion device has a housing to hold the syringe in which is provided a driving arm for driving the syringe plunger. The driving arm can be moved by means of a clockwork mechanism by which the required infusion time can be adjusted.

A disadvantage of the known infusion device is that, before the installation of the syringe and the subsequent administration of the respective liquid drug, first of all air must be evacuated from the syringe and the infusion line. This is an important reason why this device can only be used by trained staff. Furthermore, in particular because of the clockwork mechanism used, the device has relatively high production costs and is very sensitive to external influences. Moreover, the clockwork mechanism is subject to a certain wear and must be reset at certain time intervals in order to be able to ensure a precise mode of operation.

The object of the invention is to avoid the aforementioned disadvantages in a generic continuous infusion device and also to enable use by medically untrained staff and in particular by the patients themselves.

This object is achieved by a continuous infusion device having the features of claim 1. In this case the main axis of extent of the infusion appliance seat has a predetermined relief angle in relation to a horizontal support plane of the housing, wherein the outlet-side end is arranged above the ram-side end of the infusion appliance seat. As a result, the infusion appliance seat predetermines a position of the infusion appliance to be held, in which the air contained in the infusion appliance collects in a specified upper region. In this way it is ensured that when the infusion appliance is driven first of all the air escapes from the appliance or from a connected infusion line. As a result, the infusion appliance to be held in the infusion appliance seat can be vented particularly simply, so that it is possible in turn for the venting to be carried out automatically or by medically untrained staff or by the patient himself.

In an advantageous embodiment the relief angle is between 5 and 90°, so that even in the event of slight unevenness of the respective relief surface a reliable accumulation of the air contained in the infusion appliance in a predetermined upper region can be ensured.

In this case it is advantageous if the infusion appliance seat has an encoding for a specified angular position of the infusion appliance to be held, that is to say a twisting angle orthogonal to the main axis of extent, relative to the main axis of extent. As a result, in particular in an infusion appliance with eccentrically arranged outlet, such as for example a syringe opening with an eccentric syringe opening, it can be ensured that after the installation of the infusion appliance in the infusion appliance seat the outlet forms the uppermost region of the infusion appliance with respect to the gravitational direction and the contained air accumulates thereon.

Advantageously the infusion appliance seat can be moved with the ram-side end in the direction of the ram abutment/actuation element and for this purpose is coupled in terms of movement to an operating member which is movable between a closed position and an open position. As a result, in said open position the continuous infusion device enables convenient installation or removal of the infusion appliance with the ram abutment/actuation element spaced from it.

In this case it is advantageous if the operating member is part of a displacement device which, during a closing movement of a housing cover, can be driven with a driving force and as a result serves for displacement of the infusion appliance seat relative to the ram abutment/actuation element. This enables a simple coupling in terms of movement between the housing cover and the infusion appliance seat, so that by mere closure of the cover the infusion appliance seat can be brought automatically into a stop position on the ram abutment/actuation element.

In this case the displacement device advantageously has a compensating spring, by means of which it is possible to compensate for tolerances with regard to the dimensions and the filling levels of the respective infusion appliance.

In a particularly advantageous embodiment of the continuous infusion device the drive is formed predominantly by a drive spring. As a result, a purely mechanically operating drive can be provided, by means of which, regardless of a locally present power supply system or a battery power, small infusion flows of a drug can be administered continuously over several hours into the bloodstream of a patient. This enables a very flexible and, for example, mobile use of the device, and also no precautions are necessary with regard to a possible power failure or insufficient battery power during an infusion process.

In a further advantageous embodiment the control arrangement has a separate control drive spring. Due to this discrete force storage of the control arrangement it is possible to prevent feedback from the drive spring to the control arrangement, which enables a particularly exact and safe operation of the continuous infusion device.

Furthermore, it is advantageous if a self-locking means is provided between the drive and the control arrangement and can be overcome by means of a torque which can be generated by the control arrangement. Due to such a self-locking means the displacement movement of the actuator can be safely stopped by the control arrangement and as a result the respective infusion process can be ended exactly at the predetermined time.

In this case the self-locking means is advantageously formed by a worm transmission. In this case the worm transmission enables reliable inhibition of the displacement movement of the actuating device by simple means.

Moreover, it is advantageous if the control arrangement has an adjustable rotation damper, by means of which the speed of advance of the actuating device can be limited. By the use of such a rotation damper the infusion rate or the infusion time can be set particularly exactly and in a continuously variable manner.

Furthermore, the above-mentioned object is achieved by an infusion arrangement which has a continuous infusion device in one of the embodiments described above and an infusion appliance, wherein the infusion appliance is formed by an infusion syringe which is adapted in terms of size and geometry to the infusion appliance seat and has an eccentrically arranged syringe outlet. In this way it can be ensured that the air contained in the infusion appliance, in the installed state, collects on the syringe outlet arranged at the top, which enables a particularly simple or automatic venting.

In a particularly advantageous embodiment of the infusion arrangement the infusion syringe is connected to an infusion line, on the end of which is provided a hydrophobic membrane which serves for venting and is permeable to air but provides a seal against liquid. Thus, after connection of the infusion line to the syringe outlet arranged at the uppermost location on the infusion appliance, both the syringe outlet and also the infusion line can be vented by the simple application of the syringe plunger.

In this case the infusion syringe seated in the infusion appliance seat is advantageously displaceable by the closing movement of the housing cover or the displacement device towards the ram abutment/actuation element until the hydrophobic membrane is acted upon by the infusion liquid held in the container via the infusion line. In this way, solely by closure of the cover of the continuous infusion device, the automatic venting of both the infusion appliance and also the infusion line can be ensured.

Moreover, it is advantageous if a further hydrophobic membrane, which above a predetermined threshold pressure is permeable with respect to the infusion liquid, is arranged upstream of the hydrophobic membrane. Due to this upstream membrane, which is more readily permeable than the other membrane, even after the complete venting at least a slight displacement of the infusion appliance relative to the actuator is possible in order, for example, to enable fixing the infusion appliance seat in one of several latching positions.

A locking arrangement is advantageously provided, by means of which the infusion appliance seat can be fixed in relation to the housing, wherein the locking arrangement can be activated by a motion resistance which acts on the infusion appliance seat and which is generated by the liquid pressure building up between the hydrophobic membrane and the syringe plunger during the displacement of the infusion appliance against the ram abutment/actuation element. In this way the locking of the infusion appliance seat can take place automatically in each case when a vented starting position is reached.

In this case it is advantageous if the locking arrangement has a wedge gear, by means of which at least one locking element carried along on the infusion appliance seat can be brought into a locking receptacle on the housing side. In this way a stable automatic locking of the infusion appliance seat is possible by simple means.

Figure 1:
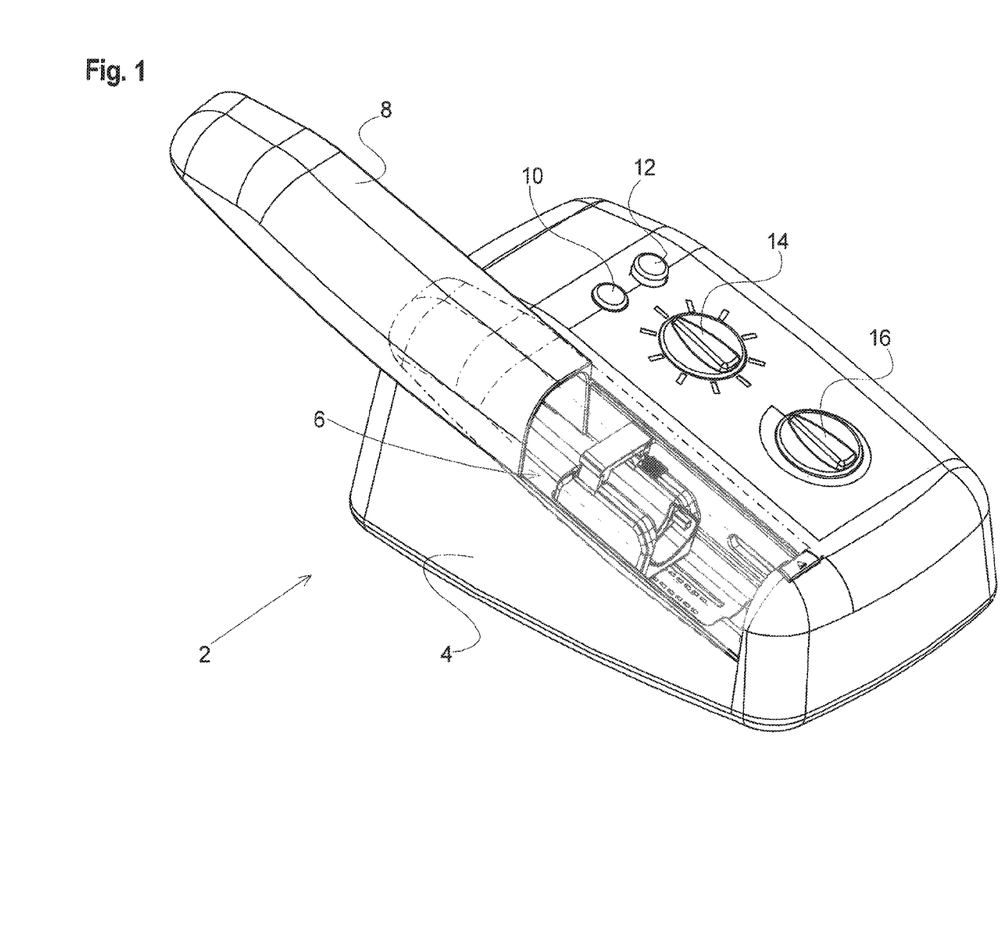
FIG. 1 shows a perspective view of a continuous infusion device according to the invention with a housing cover in the open position.

An exemplary embodiment of the invention is illustrated in the drawings, in which:

FIG. 1 shows a continuous infusion device 2, which serves for administration of small infusion flows of an infusion liquid, which is formed for example by a liquid drug against multiple sclerosis, over an extended time period of several minutes or several hours.

The continuous infusion device 2 has a housing 4 on which a displaceable infusion appliance seat 6 is provided. Furthermore, on the housing 4 a housing cover 8 is provided, by means of which the access to the infusion appliance seat 6 can be closed or freed. For this purpose, the housing cover 8 is displaceable between an illustrated open position and a closed position illustrated by dash-dot lines.

Furthermore, on the housing a plurality of operating elements are provided, by means of which the user can set a desired infusion regimen on the continuous infusion device 2 as well as starting and stopping the device. In this case the operating elements consist, for example, of a first push button 10 for starting and a second push button 12 for stopping of an infusion process as well as a first rotary switch 14 for setting a specific infusion volume and a second rotary switch 16 for setting a specific infusion rate.

Figure 2:
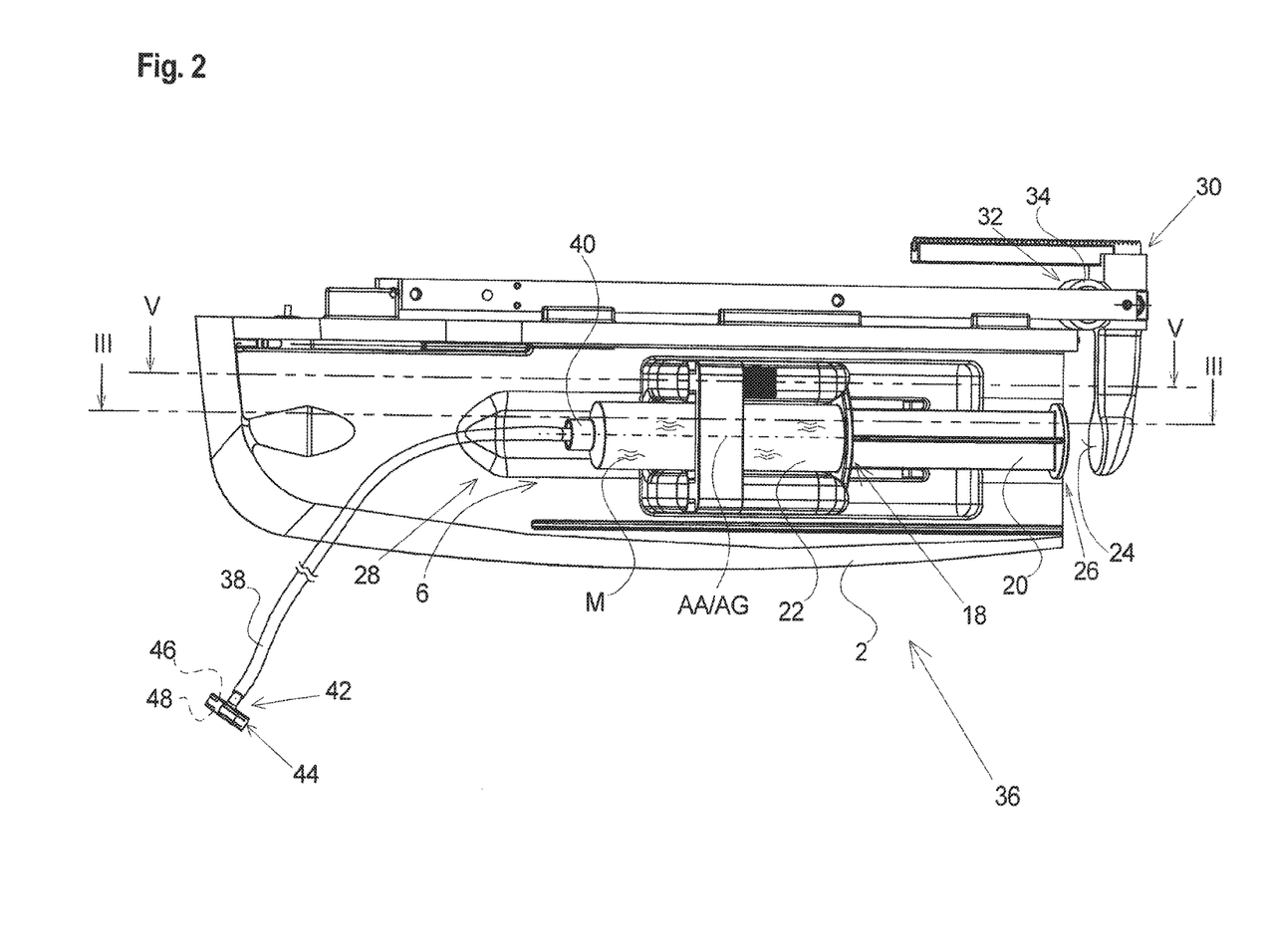
FIG. 2 shows a plan view of an infusion appliance seat of the continuous infusion device with the infusion appliance seated therein.

As can be seen from FIG. 2, the infusion appliance seat 6 serves to hold an infusion appliance 18 in the form of a syringe, which has a container 22 which can be emptied by means of a ram 20 and in which an infusion liquid to be administered in the form of a liquid drug M is received.

As can also be seen from FIG. 2, the movable infusion appliance seat 6 in the illustrated open position is arranged in such a way that the infusion appliance 18 can be seated, even with the ram 20 completely extended, distanced from a ram abutment/actuation element 24. In this case the infusion appliance seat 6 extends from a ram-side end 26 to an outlet-side end 28 along a main axis of extent AA which, in the installed state of the infusion appliance 18, corresponds to the main axis of extent AG thereof.

The ram abutment/actuation element 24 is part of an actuator 30, by means of which the infusion appliance 18 can be emptied automatically. For this purpose, the actuating device 30 has a drive 32 which is formed substantially by a drive spring 34, by means of which the ram abutment/actuation element 24 can be pressed against the ram 20 of the infusion appliance 18.

In the state illustrated in FIG. 2 with installed infusion appliance 18, the continuous infusion device 2 forms an infusion arrangement 36 which also has an infusion line 38 which is connected to a syringe outlet 40 of the infusion appliance 18 arranged at the outlet end 28 of the infusion appliance seat 6. In this case the infusion line 38 has, at a delivery end remote from the infusion appliance 18, a venting arrangement 44 in which a first hydrophobic membrane 46 and a second hydrophobic membrane 48 are provided. Both hydrophobic membranes 46, 48 act in a fundamentally air-permeable but liquid-impermeable manner. However, this impermeability to liquids can be counteracted by application of a certain liquid pressure, wherein in the case of the first membrane 46 a lower liquid pressure is necessary for this than in the case of the second membrane 48.

Figure 3:
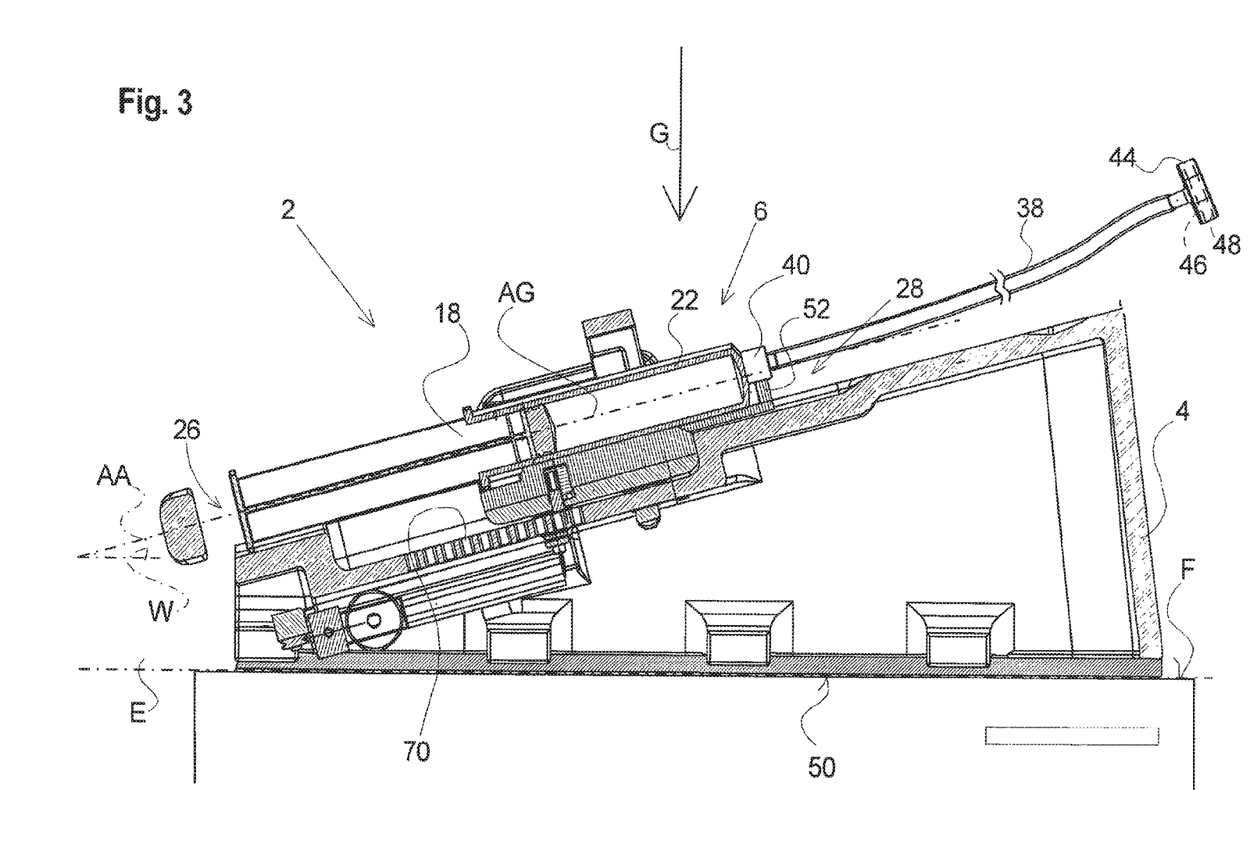
FIG. 3 shows a cross-section through the infusion appliance seat in the plane III-III in FIG. 2.

As can be seen in particular from FIG. 3, the main axis of extent AA of the infusion appliance seat 6 has a relief angle W between 5 and 90° in relation to a support plane E. In this case the support plane E is spanned by a base-side contact region 50 of the housing 4, by means of which the continuous infusion device 2 can be set down on a preferably planar horizontal resting surface F. In this case, as illustrated, the contact region 50 can be formed by a bearing plate or alternatively also, for example, by a plurality of spaced-apart contact surfaces or positioning feet. In any case, due to the relief angle W provided, at least with a substantially horizontal orientation of the support plane E, the outlet-side end 28 of the infusion appliance seat 6 is positioned by means of the ram-side end 26.

As can also be seen from FIG. 3, the syringe outlet 40 of the infusion appliance 18 is, for example, eccentric with respect to the main axis of extent AG. In this case at the outlet-side end 28 encoding means 52 are provided which encode the infusion appliance seat 6 relative to the infusion appliance 18 in such a way that, in relation to the main axis of extent AA, this appliance can be inserted into the infusion appliance seat 6 only in the illustrated angular position, in which the syringe outlet 40 is arranged in the maximum uppermost position with respect to the gravitational direction G.

In this way it is ensured that air coming from the seated infusion appliance 18 and contained in the container 22 accumulates at the syringe outlet 40 and, when the ram 20 is actuated, is displaced further via the infusion line 38 before the flow front of the liquid drug to the venting arrangement 44, where the air can exit via the hydrophobic membranes 46, 48. To this end the free flow cross-section of the infusion line 38 is dimensioned so that the surface tension of the infusion liquids provided for administration is sufficient in any case in order to prevent the flow front thereof within the infusion line from being able to move past air bubbles contained therein.

Figure 4:
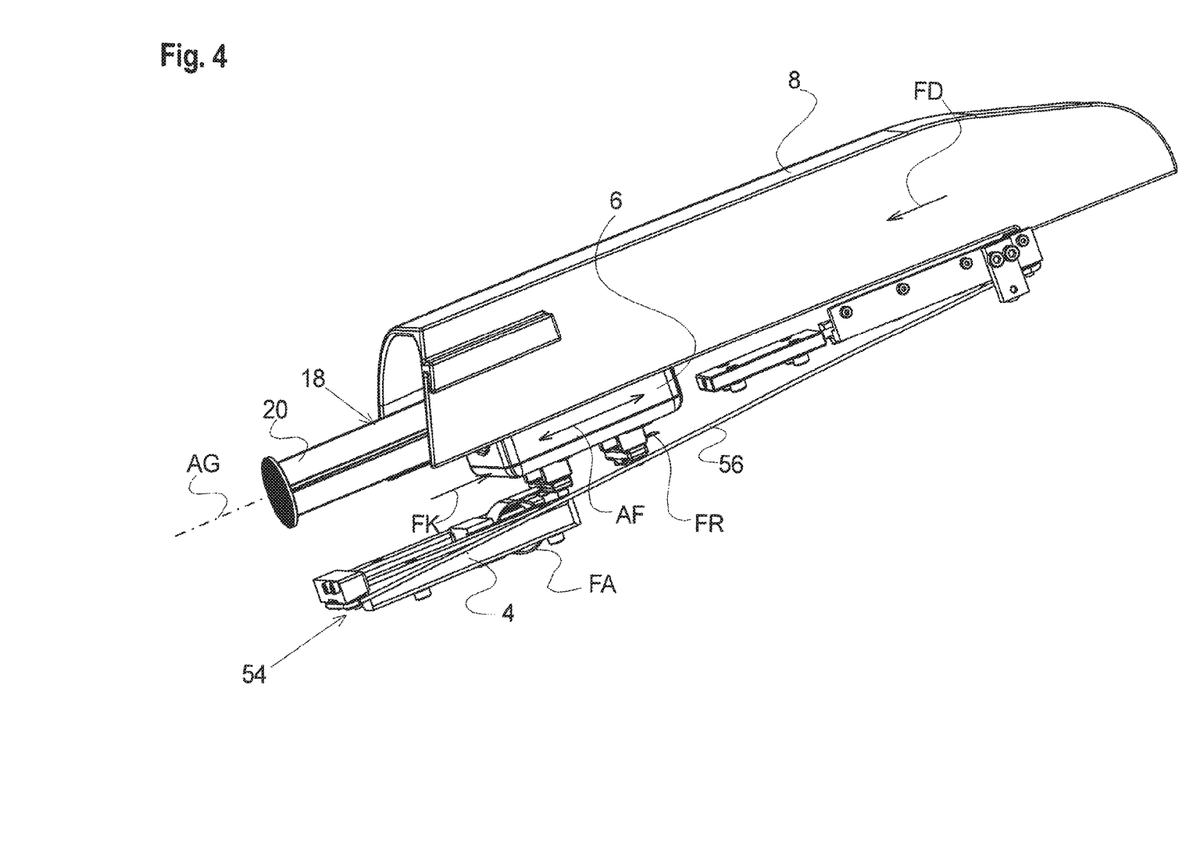
FIG. 4 shows a perspective view of a separately illustrated displacement device of the continuous infusion device according to FIG. 1.

In order to be able to bring the infusion appliance seat 6, with the filled infusion appliance 18 seated thereon, automatically into a starting position, in which the ram 20 contacts the ram abutment/actuation element 24 of the actuating device 30 and both the infusion appliance 18 and also the infusion line 38 is vented, a displacement device 54 is provided, as can be seen from FIG. 4. This has a traction cable 56 which connects the housing cover 8 to the infusion appliance seat 6. In this case the traction cable 56 is redirected on the housing 4 in such a way that, during the displacement of the housing cover 8 from the open position into the closed position by means of a force FD applied thereto, the infusion appliance seat 6 is driven with a driving force AF which displaces it against a spring force FK of a restoring spring FR in the direction of the ram abutment/actuation element 24. The housing cover 8 itself acts as operating member of the displacement device 54, driving the displacement of the infusion appliance seat 6. As an alternative to this, the displacement device 54 can also have a separate operating member, which is either displaceable by the closing movement of the housing cover 8 or is designed separately from the housing cover 8 and can be actuated independently thereof (not shown).

When the housing cover 8 is displaced out of the closed position into the open position, the infusion appliance seat 6 on the other hand is driven by the resilient restoring forces of the restoring spring FR, which is biased in the closed position, with the driving force AF now directed in the opposing direction, so that the infusion appliance seat 6 is moved away from the ram abutment/actuation element 24 again.

Furthermore, a compensating spring FA is arranged between the traction cable 56 and the infusion appliance seat 6. This serves to compensate for different longitudinal extents of the infusion appliances 18 used along their respective main axis of extent AG, which for example are due to different filling levels of the container 22. Moreover, pressure peaks which may be produced, for example, during jerky closure of the housing cover 8 can be compensated for by the compensating spring FA.

Figure 5A:
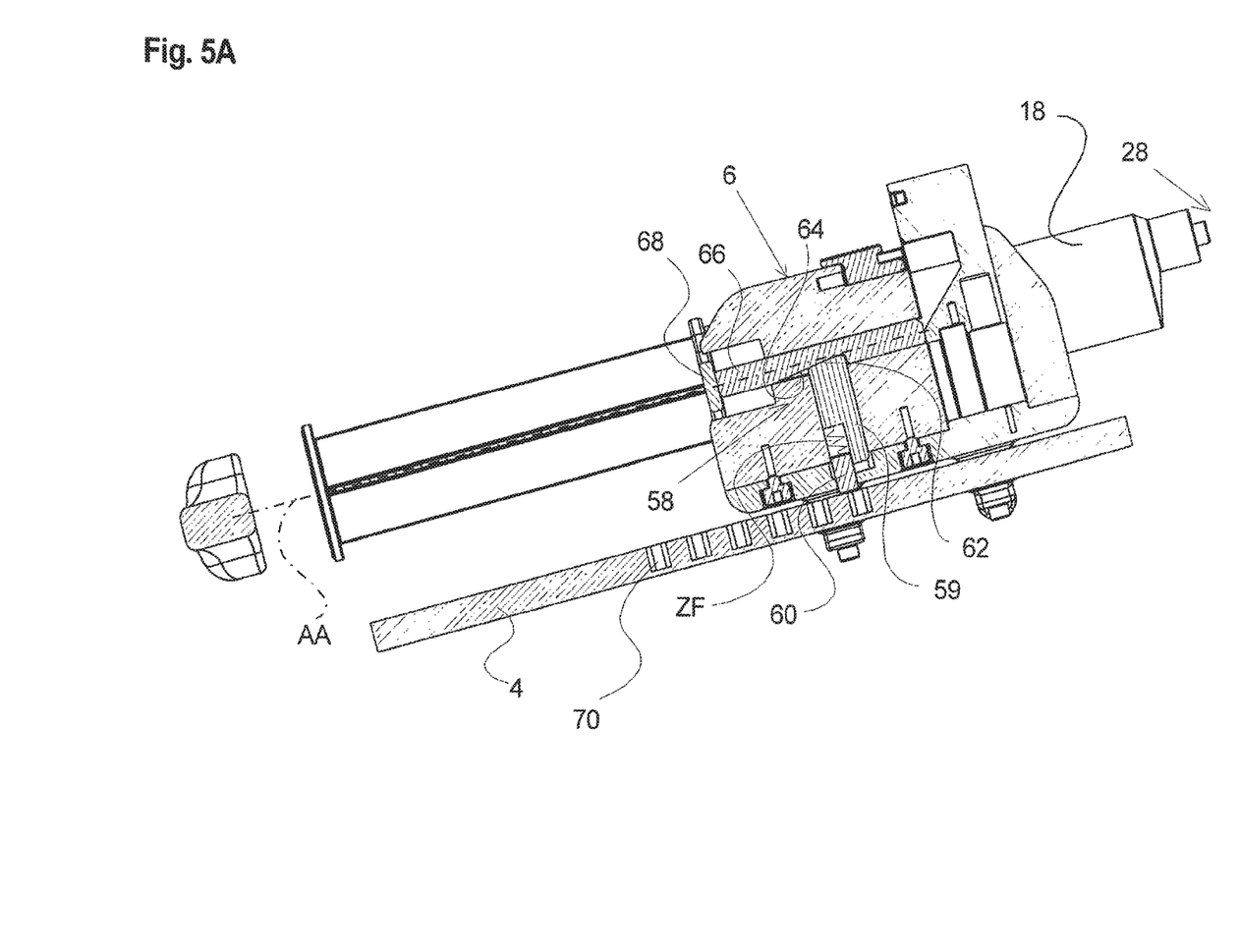
FIG. 5A shows a cross-section through the infusion appliance seat in the plane V-V in FIG. 2 in a passive position of a locking arrangement.

In order to fix the infusion appliance seat 6 with the infusion appliance 18 seated thereon in the vented starting position, a locking arrangement is provided which has a wedge gear 58 carried along on the infusion appliance seat 6, as illustrated in FIG. 5A. The wedge gear has an intermediate element 59, on which a locking element 60 is supported with an intermediate spring ZF interposed, and is held on the infusion appliance seat 6 so as to be movable transversely to the main axis of extent AA.

In the open position of the housing cover 8, as illustrated, this locking element 60 is initially arranged in an engaged passive position. In this position a rear end 62 of the intermediate element 59 rests on a slide region 64, cut out in the form of a ramp, of an operating element 66 which is mounted movably in the direction of the main axis of extent AA relative to the locking element 60. A syringe collar 68 of the infusion appliance 18 seated in the infusion appliance seat 6 rests on an outer end of the operating element 66.

Figure 5B:
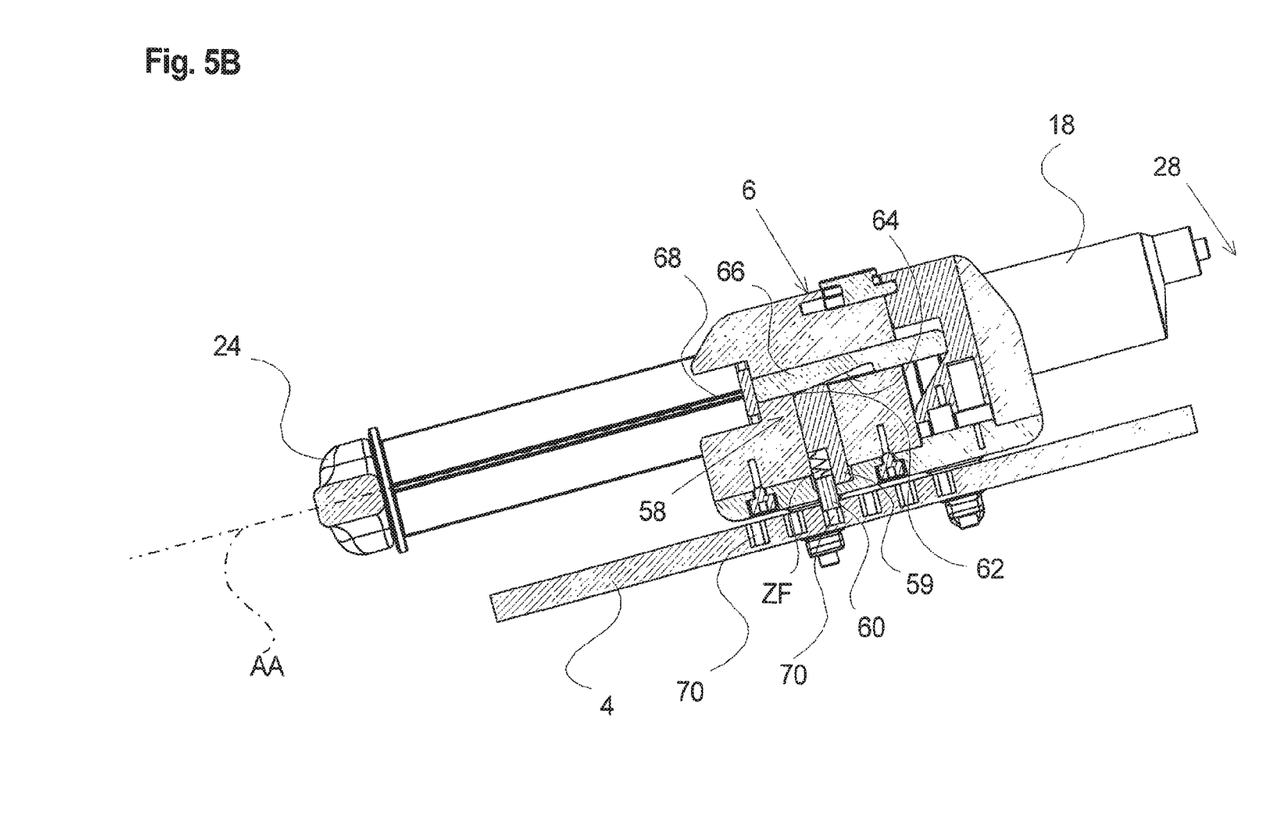
FIG. 5B shows a cross-section through the infusion appliance seat in an active position of the locking arrangement according to FIG. 5A.

As a result, when the ram 20 is driven by the ram abutment/actuation element 24 the operating element 66 can be driven by means of the syringe collar 68 with a force which displaces it in the direction of the outlet end 28. In this case the operating element 66 presses by means of the slide region 64 against the rear end 62 of the intermediate element 59, so that this latter is moved downwards. In this case the intermediate element 59 in turn drives the locking element 60 by means of the intermediate spring ZF, the locking element being biased against a region of the housing 4 into which a plurality of locking receptacles 70 are introduced. As soon as, during the displacement of the infusion appliance seat 6, the locking element 60 is positioned precisely above one of these locking receptacles 70, the locking element is displaced from the illustrated passive position into an active position in which it engages in the locking receptacle 70, as illustrated in FIG. 5B.

Figure 6:
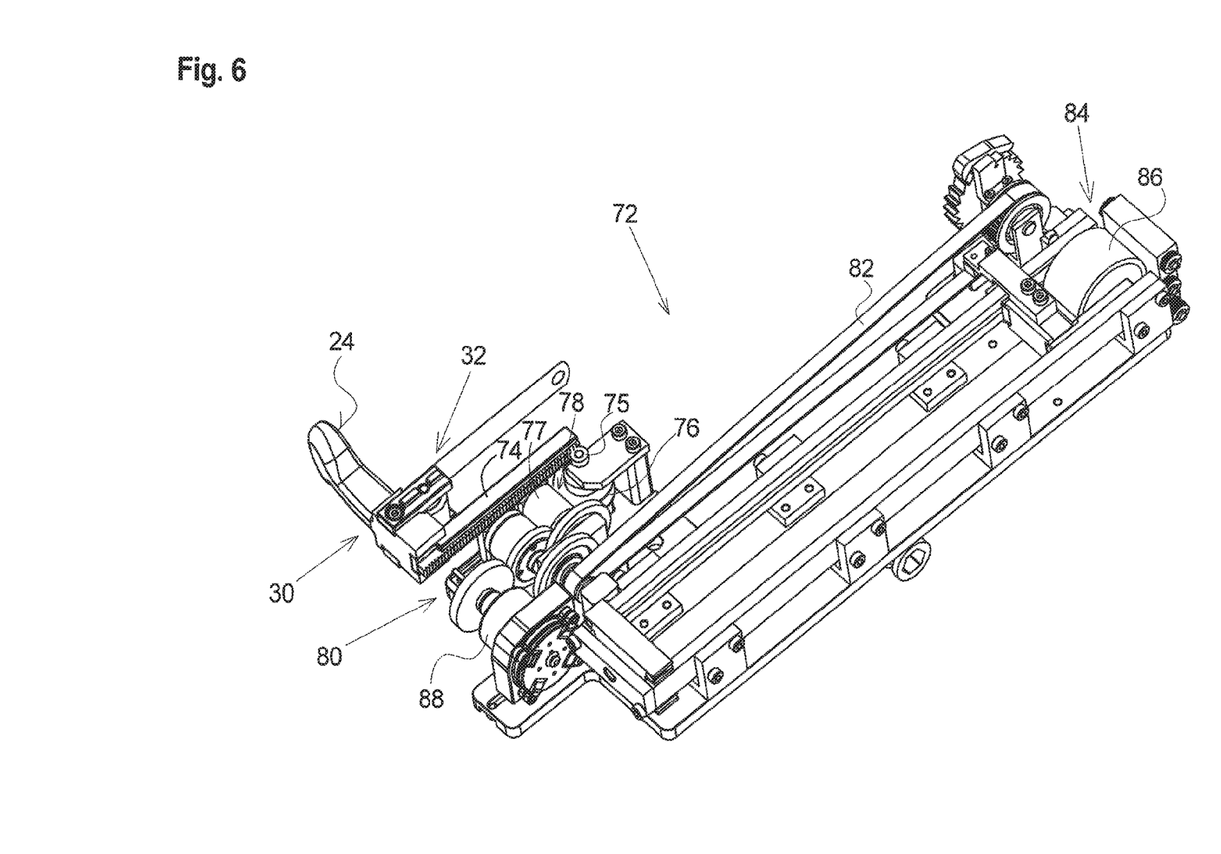
FIG. 6 shows a perspective view of a separately illustrated control arrangement of the continuous infusion device according to FIG. 1.

In order now, in this locked starting position of the infusion appliance 18, to be able to carry out the infusion in a specified manner, the continuous infusion device 2 has, in addition to the actual drive 32, a control arrangement 72 which is illustrated in FIG. 6. By means of this control arrangement 72 a required speed of advance of the actuator 30 or the ram abutment/actuation element 24 thereof can be set.

For this purpose, the actuator 30 has a toothed rack 74 which meshes with a gear 75 connected by means of a shaft to a worm gear 76 of the control arrangement. In this case the worm gear 76 forms with a worm element 77 a self-locking worm transmission 78, the self-locking of which can be cancelled by a control transmission 80 which co-operates with the worm element 77. In this case the control transmission 80 can be driven, for example, by means of a toothed belt 82 with a torque, wherein the toothed belt 82 in turn is driven by a spring force storage device 84 with a discrete control drive spring 86.

Thus the actuator 30 is actually driven solely by the drive spring 34, wherein the speed of advance of the driven ram abutment/actuation element 24 applicable here depends upon the speed at which the worm transmission 78 rotates.

In this case a rotary damper 88, which can be adjusted by the user by means of the second rotary switch 16, is provided on the control transmission 80 for continuously variable adjustment of the required speed of advance.

Accordingly, a conventional infusion process proceeds as follows:

In the open position of the housing cover 8 according to FIG. 1, the infusion appliance 18 filled with the liquid drug M to be administered is inserted into the infusion appliance seat 6 and according to FIGS. 2 and 3 is connected to the infusion line 38 and the venting arrangement 44 provided thereon.

By movement of the housing cover 8 into the closed position, the infusion appliance seat 6 is driven by means of the traction cable 56 with the driving force AF and is displaced in the direction of the ram abutment/actuation element 24. As soon as the ram 20 of the infusion appliance 18 is pressed against the ram abutment/actuation element 24, the liquid drug contained in the container 22 is transported into the infusion line 38 by means of the syringe outlet 40. In this case the air in the container 22 and the infusion line 38 is transported to the venting arrangement 44 and can escape here to the outside via the membranes 46, 48.

However, as soon as the ram 20 is pushed into the container 22 so far that the air has completely escaped and now the liquid drug M is present on the first hydrophobic membrane 46, by means of the liquid a pressure resistance builds up which counteracts the moving force acting on the ram 20, so that in turn the operating element 66 of the wedge gear 58 (see FIG. 5) is driven by a force and is displaced thereby relative to the locking element 60. In this case the slide region 64 presses against the rear end 62 and thereby moves the intermediate element 59, so that in turn the locking element 60 is pretensioned against the housing 4.

If in this case, in spite of the fully inserted operating element 66, the locking element 60 still cannot engage in any locking receptacle 70, small amounts of the liquid drug M escape on the first hydrophobic membrane 46 due to the increased liquid pressure, so that the infusion appliance seat 6 can move at least slightly further in the direction of the ram abutment/actuation element 24. This further displacement takes place until the locking element 60 engages in one of the locking receptacles 70 introduced into the housing 4. In this position the infusion appliance seat 6 with the infusion appliance 18 seated thereon is fixed relative to the housing 4 and both the container 22 and also the infusion line 38 are vented.

At the latest, in this condition the amount to be administered and the duration or the speed of the infusion process can now be determined by means of the rotary switches 14, 16. Moreover, the venting arrangement 44 can now be removed and the infusion line 38 can be connected, for example, to a catheter (not shown).

The toothed belt 82, which is driven by the previously wound control drive spring 86, is then freed (see FIG. 6) by actuation of the push button 10. This belt in turn drives the control transmission 80, which as a function of the speed set by means of the rotation damper 88 or by means of the rotary switch 16 drives the worm gear 76 by application of a torque.

The self-locking of the worm transmission 78 is cancelled by this torque, so that now even the toothed rack 74 of the actuator 30 can be displaced as a function of the speed set on the control arrangement 72. In this case the actuator 30 is driven by the previously tensioned drive spring 34, by means of which the ram abutment/actuation element 24 is pressed against the ram 20.

Since the rest of the infusion appliance 18 is fixed to the housing 4 by means of the locked infusion appliance seat 6, the liquid drug M stored in the container 22 is transported by the pressurized ram 20 into the infusion line 38 until the infusion amount set on the control arrangement is reached or the push button 12 is pressed in order to stop the infusion process. In both cases the driving of the control transmission 80 by means of the toothed belt 82 is ended, and as a result, the self-locking on the worm transmission 78 is restored.

The invention claimed is:

1. A device for continuous infusions comprising:
a housing having a base, the base of the housing configured to be set down on a planar horizontal resting surface during use,
an infusion appliance seat disposed in the housing for receiving an infusion appliance with at least one container that can be pressed empty by a ram, the infusion appliance seat extending along a main axis, and configured to support the infusion appliance from a ram-side end to an outlet-side end of the infusion appliance,
an actuator for automatically emptying the infusion appliance,
a drive for moving a ram abutment/actuation element of the actuator, and
a control arrangement by which a speed of advance of the actuator is adjustable,
wherein the main axis of extent of the infusion appliance seat has a predetermined relief angle in relation to a support plane of the housing, so as to cause a main axis of extent of the infusion appliance to have the same predetermined relief angle as the infusion appliance seat in relation to the support plane, the support plane being coplanar with the base of the housing,
wherein the infusion appliance seat is disposed above the base of the housing during use, and
wherein the outlet-side end is arranged above the ram-side end of the infusion appliance seat with respect to the support plane.

2. The continuous infusion device according to claim 1, wherein the relief angle is between 5 and 90°.

3. The continuous infusion device according to claim 1, wherein the infusion appliance seat has an encoding mechanism that sets a specified angular position of the infusion appliance to be seated with respect to the main axis of extent.

4. The continuous infusion device according to claim 1, wherein the infusion appliance seat is coupled to an operating member which is movable between a closed position and an open position such that the infusion seat can be moved with the ram-side end in the direction of the ram abutment/actuation element.

5. The continuous infusion device according to claim 4, wherein the operating member is part of a displacement device which, during a closing movement of a housing cover, can be driven with a driving force (AF).

6. The continuous infusion device according to claim 5, wherein the displacement device has a compensating spring to compensate for tolerances.

7. The continuous infusion device according to claim 1, wherein the drive comprises a drive spring.

8. The continuous infusion device according to claim 1, wherein the control arrangement has a control drive spring.

9. The continuous infusion device according to claim 7, further comprising a self-locking means provided between the drive and the control arrangement, wherein the self-locking means can be unlocked by a torque generated by the control arrangement.

10. The continuous infusion device according to claim 9, the self-locking means comprises a worm transmission (78).

11. The continuous infusion device according to claim 1, the control arrangement has an adjustable rotation damper that is configured to limit the speed of advance of the actuator.

12. An infusion arrangement with a continuous infusion device according to claim 1, wherein the infusion appliance comprises an infusion syringe which is configured in terms of size and geometry to fit into the infusion appliance seat and has an eccentrically arranged syringe outlet with respect to the main axis of extent.

13. The infusion arrangement according to claim 12, wherein the infusion syringe is connected to an infusion line, on the end of which is provided a hydrophobic membrane which serves for venting and is permeable to air but provides a seal against liquid.

14. A device for continuous infusions comprising:
a housing having a base, the base of the housing configured to be set down on a planar horizontal resting surface during use,
an infusion appliance seat disposed in the housing for receiving an infusion appliance with at least one container that can be pressed empty by a ram, the infusion appliance seat extending along a main axis of extent from a ram-side end to an outlet-side end,
an actuator for automatically emptying the infusion appliance,
a drive for moving a ram abutment/actuation element of the actuator, and
a control arrangement by which a speed of advance of the actuator is adjustable,
wherein the main axis of extent of the infusion appliance seat has a predetermined relief angle in relation to a support plane of the housing, the support plane being coplanar with the base of the housing,
wherein the infusion appliance seat is disposed above the base of the housing during use,
wherein the outlet-side end is arranged above the ram-side end of the infusion appliance seat with respect to the support plane,
wherein the infusion appliance comprises an infusion syringe which is configured in terms of size and geometry to fit into the infusion appliance seat and has an eccentrically arranged syringe outlet with respect to the main axis of extent,
wherein the infusion syringe is connected to an infusion line, on the end of which is provided a hydrophobic membrane which serves for venting and is permeable to air but provides a seal against liquid, and
wherein the infusion syringe seated in the infusion appliance seat is displaceable by the closing movement of the housing cover or the displacement device towards the ram abutment/actuation element until the hydrophobic membrane is acted upon by the infusion liquid held in the container via the infusion line.

15. The infusion arrangement according to claim 13, further comprising a further hydrophobic membrane, which above a predetermined threshold pressure is permeable with respect to the infusion liquid, arranged upstream of the hydrophobic membrane).

16. A device for continuous infusions comprising:
a housing having a base, the base of the housing configured to be set down on a planar horizontal resting surface during use,
an infusion appliance seat disposed in the housing for receiving an infusion appliance with at least one container that can be pressed empty by a ram, the infusion appliance seat extending along a main axis of extent from a ram-side end to an outlet-side end,
an actuator for automatically emptying the infusion appliance,
a drive for moving a ram abutment/actuation element of the actuator, and
a control arrangement by which a speed of advance of the actuator is adjustable,
wherein the main axis of extent of the infusion appliance seat has a predetermined relief angle in relation to a support plane of the housing, the support plane being coplanar with the base of the housing,
wherein the infusion appliance seat is disposed above the base of the housing during use,
wherein the outlet-side end is arranged above the ram-side end of the infusion appliance seat with respect to the support plane,
wherein the infusion appliance comprises an infusion syringe which is configured in terms of size and geometry to fit into the infusion appliance seat and has an eccentrically arranged syringe outlet with respect to the main axis of extent,
wherein the infusion syringe is connected to an infusion line, on the end of which is provided a first hydrophobic membrane which serves for venting and is permeable to air but provides a seal against liquid,
further comprising a second hydrophobic membrane, which above a predetermined threshold pressure is permeable with respect to the infusion liquid, arranged upstream of the hydrophobic membrane, and
further comprising a locking arrangement to fix the infusion appliance seat in relation to the housing, wherein the locking arrangement is configured to be activated by a motion resistance which acts on the infusion appliance seat and which is generated by the liquid pressure building up between the hydrophobic membrane and the syringe plunger during the displacement of the infusion appliance against the ram abutment/actuation element.

17. The infusion arrangement according to claim 16, wherein the locking arrangement has a wedge gear, by means of which at least one locking element carried along on the infusion appliance seat can be brought into a locking receptacle on the housing side.

18. A device for continuous infusions comprising:
a housing having a base, the base of the housing configured to be set down on a planar horizontal resting surface during use,
an infusion appliance seat disposed in the housing for receiving an infusion appliance with at least one container that can be pressed empty by a ram, the infusion appliance seat extending along a main axis, and configured to support the infusion appliance from a ram-side end to an outlet-side end of the infusion appliance,
an actuator for automatically emptying the infusion appliance, a drive for moving a ram abutment/actuation element of the actuator, and a control arrangement by which a speed of advance of the actuator is adjustable, wherein the main axis of extent of the infusion appliance seat has a predetermined relief angle in relation to a support plane of the housing, so as to cause a main axis of extent of the infusion appliance to have the same predetermined relief angle as the infusion appliance seat in relation to the support plane, wherein the outlet-side end is arranged above the ram-side end of the infusion appliance seat, wherein the infusion appliance comprises an infusion syringe which is configured in terms of size and geometry to fit into the infusion appliance seat and has an eccentrically arranged syringe outlet with respect to the main axis of extent, and wherein the infusion syringe is connected to an infusion line, on the end of which is provided a hydrophobic membrane which serves for venting and is permeable to air but provides a seal against liquid.

* * * * *